United States Patent [19]
Maurizio

[11] Patent Number: 5,353,974
[45] Date of Patent: Oct. 11, 1994

[54] SURGICAL NEEDLE SYSTEM

[76] Inventor: Cortale Maurizio, Via Lovisato, Trieste, Italy, 34100

[21] Appl. No.: 72,996
[22] Filed: Jun. 7, 1993
[51] Int. Cl.⁵ .......................................... A45C 11/00
[52] U.S. Cl. .................................. 224/219; 224/183; 224/221; 224/222
[58] Field of Search ............... 224/175, 183, 217, 218, 224/219, 221, 222, 267; 128/DIG. 6; 606/222; 335/278, 285, 286, 287, 291, 292, 293, 294; 269/8

[56] References Cited

U.S. PATENT DOCUMENTS

| | | |
|---|---|---|
| 2,164,623 | 4/1939 | Posner . |
| 2,176,052 | 10/1939 | Beyer ................. 224/183 X |
| 2,266,230 | 12/1941 | Mazzco et al. ............ 128/DIG. 6 |
| 2,449,882 | 9/1948 | Daniels . |
| 2,491,860 | 12/1949 | Ingraham ............... 335/285 |
| 2,525,398 | 10/1950 | Collins ................ 224/222 X |
| 2,605,032 | 7/1952 | Hunt et al. . |
| 2,713,609 | 7/1955 | Niklason . |
| 2,824,681 | 2/1958 | Sorkin ................. 224/183 X |
| 2,907,085 | 10/1959 | Bosland . |
| 3,104,435 | 9/1963 | Beuck . |
| 3,178,784 | 4/1965 | Krauthamer . |
| 3,755,857 | 9/1973 | Simoneaux . |
| 4,514,882 | 5/1985 | Lavielle . |
| 4,606,484 | 8/1986 | Winter et al. ............... 224/218 |
| 4,770,008 | 9/1988 | Yamamura ............... 224/175 X |
| 4,847,729 | 7/1989 | Hee .................. 224/175 X |
| 5,201,444 | 4/1993 | Simonet ................ 224/183 |
| 5,235,567 | 8/1993 | Goodwin ............... 224/175 X |

Primary Examiner—Henry J. Recla
Assistant Examiner—David J. Walczak
Attorney, Agent, or Firm—Richard C. Litman

[57] ABSTRACT

A wrist attachable holder for releasably engaging a surgeon's needle so as to reduce the risk of accidental needle strikes. The holder includes a flexible bracelet adapted to be severed at one end so as to be adjustable to fit the wrist of a surgeon. The holder further includes a support body for supporting a needle. In one embodiment, a magnetic plate is embedded in a support body for magnetically retaining the needle. In another embodiment, the support body includes a set of spaced apart prongs for engaging the needle. In both embodiments, the support body is provided with a shank that terminates in a ball which is rotatably mounted in the holder. The ball arrangement permits the support body and associated magnet or pair of prongs to be positioned in a vertical plane perpendicular to the upper surface of the holder. A threaded set screw is engageable with the ball to fix the ball in a desired position and, in turn, retain the magnet or prongs and a needle associated therewith in a desired position.

16 Claims, 3 Drawing Sheets

SURGICAL NEEDLE SYSTEM

BACKGROUND OF THE INVENTION

1. Field of the Invention

The present invention relates generally to surgery and, more particularly, to a wrist attachable holder for releasably engaging a surgeon's needle so as to aid in reducing the risk of accidental needle strikes.

2. Description of the Prior Art

Doctors and surgeons have become increasingly susceptible to the hazards associated with accidental needle strikes occurring when closing a wound of a patient. It has been found that infectious deceases can be transmitted through the handling of needles in the course of stitching a wound closed. Accidents caused by inadvertent needle pricks may require blood tests for diseases, such as AIDS and hepatitis. The corresponding cost and inefficiencies associated with these tests could result in considerable waste, which may be particularly damaging to a health care facility which is striving to cut costs.

There is a need to protect healthcare professionals from inadvertently sticking themselves with a contaminated needle. The present invention reduces the risk of such occurrences. The present invention is a wrist attachable holder for releasably engaging a surgeon's needle. The holder may be in the form of a magnet for magnetically engaging the needle or may be in the form of a set of spaced apart prongs for tightly receiving the needle therebetween. In either embodiment, the holder may be retractable so as to be assume a low-profile when not in use. The retraction may be accomplished through the employment of a pivotal arrangement.

Magnetic holders have been the subject of earlier patents, such as U.S. Pat. No. 2,164,623, issued Jul. 4, 1939 to Alfred E. Posner, and U.S. Pat. No. 3,755,857, issued Sep. 4, 1973 to Curtis J. Simoneaux. Both Posner and Simoneaux disclose a wrist encircling bracelet having a magnetic plate secured thereto. Posner teaches of the plate being secured by a screw and Simoneaux describes the plate being secured by adhesive. Another magnetic holder for holding articles is disclosed in U.S. Pat. No. 2,907,085, issued Oct. 6, 1959 to James M. Bosland. Unlike Posner and Simoneaux, Bosland shows a pivotally mounted magnetic holder. Yet another magnetic holder in disclosed in U.S. Pat. No. 3,178,784, issued Apr. 20, 1965 to Charles Krauthamer who shows a magnet having a pressure sensitive adhesive surface.

A wrist attachable medical holder is disclosed in U.S. Pat. No. 2,449,882, issued Sep. 21, 1948 to Amy J. Daniels. Although not shown to be attachable to the wrist, U.S. Pat. No. 2,605,032, issued Jul. 29, 1952 to David L. Hunt et al., shows a pin holder which is removably mountable.

An article holder having a pivotal arrangement is shown in U.S. Pat. No. 2,713,609, issued Jul. 19, 1955 to Don D. Niklason. Niklason shows a ball and socket pivotal connection fixed in place by a threaded set screw.

Other patents which may be deemed of interest include U.S. Pat. No. 3,104,435, issued Sep. 24, 1963 to Coin J. Beuck, showing an article holder, and U.S. Pat. No. 4,514,882, issued May 7, 1985 to Christian Lavielle, showing a plastic clasp having flexible hinges which are severable.

None of the above patents, taken either singly or in combination, is seen to describe the instant invention as claimed.

SUMMARY OF THE INVENTION

The present invention relates to a wrist attached holder for releasably engaging a surgeon's needle so as to reduce the risk of accidental needle punctures of a surgeon's fingers while handling the needle. The holder includes a flexible bracelet adapted to be severed at one end so as to be adjustable to fit the wrist of a surgeon. The holder includes a support body for supporting a needle. In one embodiment, a magnetic plate is embedded in a support body. In another embodiment, the support body includes a set of spaced apart prongs for frictionally engaging the needle. In both embodiments, an end surface of the support body is provided with a shank. The shank terminates in a ball which is rotatably mounted in the holder so that the support body and associated magnet can be positioned in a vertical plane perpendicular to the upper surface of the holder. A threaded set screw is rotatably mounted in the holder which has sufficient length so as to be engageable with the ball to fix the ball in a desired position and, in turn, retain the magnet or prongs and a needle associated therewith in a desired position. The bracelet has portions of reduced cross-section to facilitate in flexing of the bracelet.

Accordingly, it is a principal object of the invention to provide a wrist attachable holder for releasably engaging a surgeon's needle so as to reduce the risk of accidental needle punctures of a surgeon's fingers while handling a needle.

It is another object that the holder include a flexible bracelet adapted to be severed at one end so as to be adjustable to fit the wrist of a surgeon.

It is a further object that the holder include a magnetic plate which is embedded in a support body or, alternatively, a pair of spaced apart prongs for releasably engaging the needle.

Yet another object is that the support body have an end surface which is provided with a shank which terminates in a ball which is rotatably mounted in the holder so that the support body and associated magnet or prongs can be positioned in a vertical plane perpendicular to the upper surface of the holder.

Another object is to provide a threaded set screw which is rotatably mounted in the holder and which has sufficient length so as to engage the ball to fix the ball in a desired position and, in turn, to retain the magnet or the pair of prongs and associated needle in a desired position.

Still another object is that the bracelet have portions of reduced cross-section to facilitate flexing of the bracelet.

Another objective is that the holder have a lower surface which is covered with pressure sensitive adhesive and a removable protective plastic film, wherein the protective plastic film is removable to expose the adhesive so that the holder, when positioned in a desired location on the wrist of the surgeon, is held in contact with the wrist via the adhesive.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
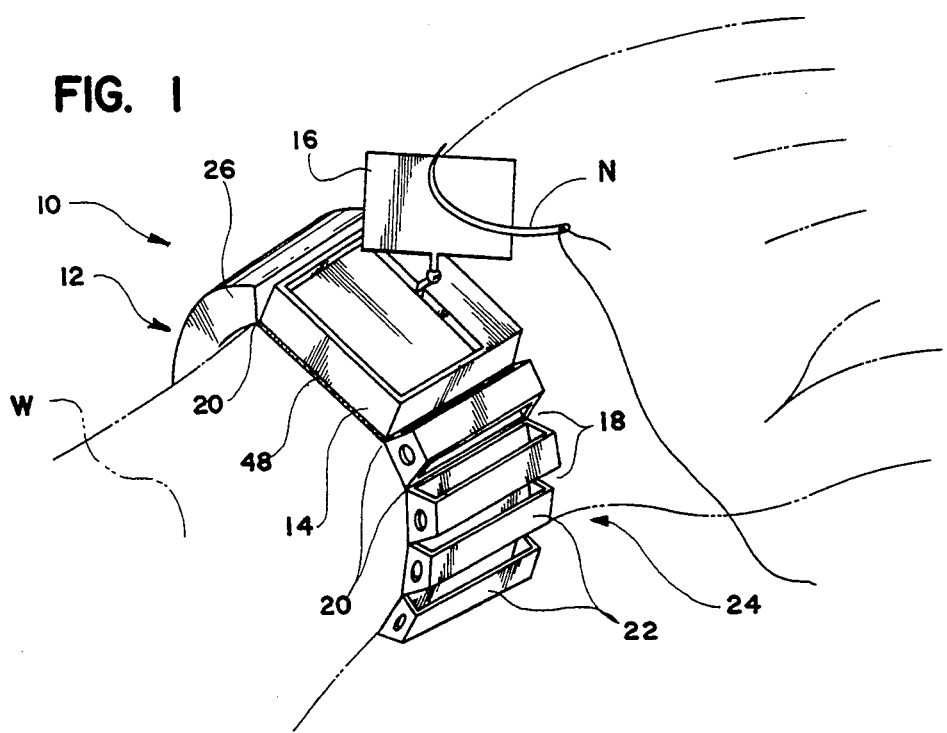
FIG. 1 is an environmental perspective view of a surgical needle system according to the present invention.

The present invention is a surgical needle system 10 for releasably engaging a surgeon's needle. As shown in FIG. 1, the surgical needle system 10 includes a bracelet 12 which is attachable to the wrist W of a surgeon, a holder 14 supported by the bracelet 12, and a support body 16 connected to the holder 14. The support body 16 is configured to releasably engage the surgeon's needle N to reduce the risk of accidental needle strikes of a surgeon's fingers (not shown) while handling the needle N.

Figure 2:
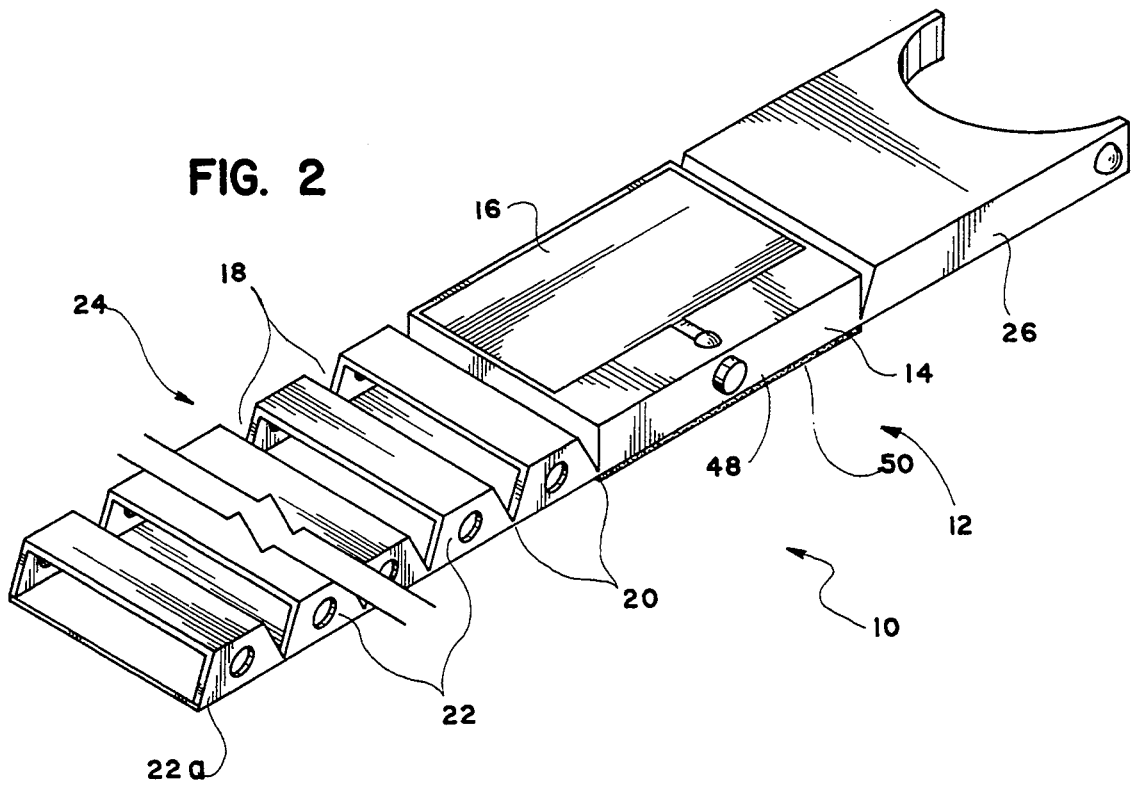
FIG. 2 is a perspective view of the surgical needle system shown in FIG. 1.
Figure 3:
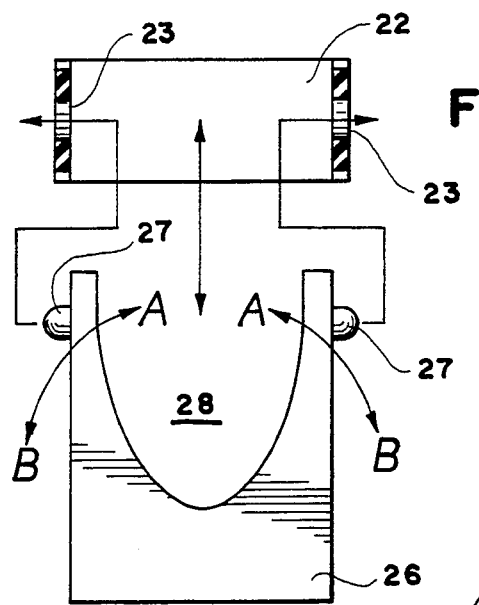
FIG. 3 is a detail view of the bracelet fastening arrangement.
Figure 4:
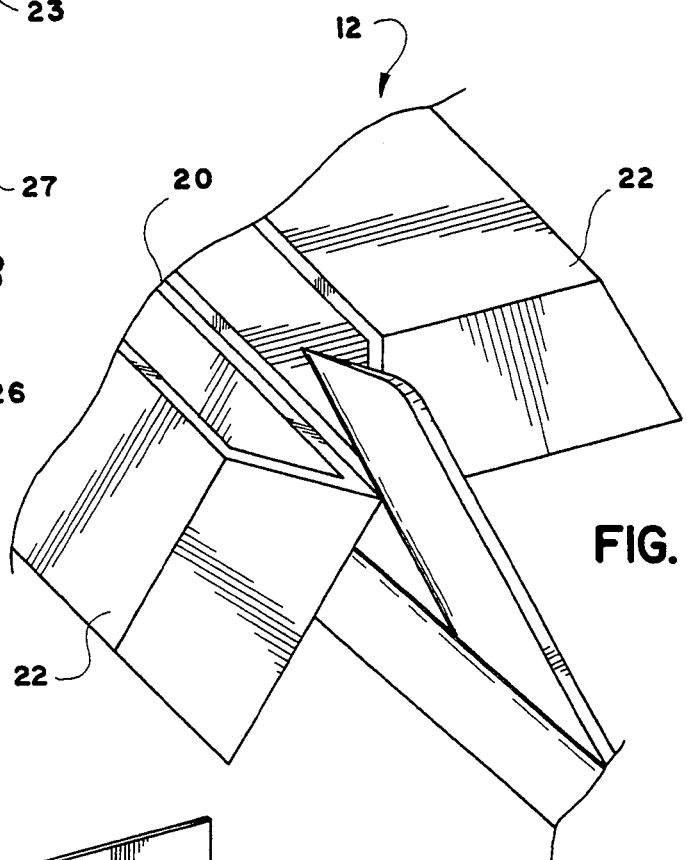
FIG. 4 is a detail view showing the flexing and severing of the end portions of the bracelet so as to adjust the length of the bracelet.

Referring to FIGS. 1 and 2, the bracelet 12 has portions or areas of reduced cross-section 18 each forming a living hinge 20 to facilitate in the flexing of the bracelet 12. The bracelet 12 further includes a plurality of separate and independent female connecting members 22 each joined to one another by a respective living hinge 20 to form a series of female connecting members 22 or a wrist strap 24. The wrist strap 24 is, in turn, joined to a first lateral end of the holder 16 by a living hinge 20. The bracelet 12 also includes a male connecting member 26 joined to a within the frame 29. The removal of the magnetic plate 30 permits second lateral end of the holder 14 by yet another living hinge 22. As shown in FIG. 3, the male connecting member 26 is-configured to matingly engage a selected one of the female connecting members 22 and, more particularly, to engage the female connecting member 22a at the terminal end of the wrist strap 24. Each of the female connecting members 22 includes opposingly disposed apertures 23 located in the longitudinal walls thereof. Opposingly directed nodules 27 are located along the longitudinal walls of the male connecting member 26. The male connecting member 26 is further provided with a cut-out 28 which permits the longitudinal walls thereof to be displaced in the directions A upon engaging the same with the female connecting member 22a. When a full engagement of the connecting members 22 and 26 is accomplished, the nodules 27 are received by the apertures 23 and the longitudinal walls of the male connecting member 26 return in the directions B to an initial or normal position. As shown in FIG. 4, the bracelet 12 is adaptable to be severed along any one of the living hinges 20 to permit the removal of any number of the female connecting members 22 and thus permit the length of wrist strap 24 to be adjusted, in turn, permitting the overall length of the bracelet 12 to be adjusted to fit the wrist W of the surgeon.

Figure 5:
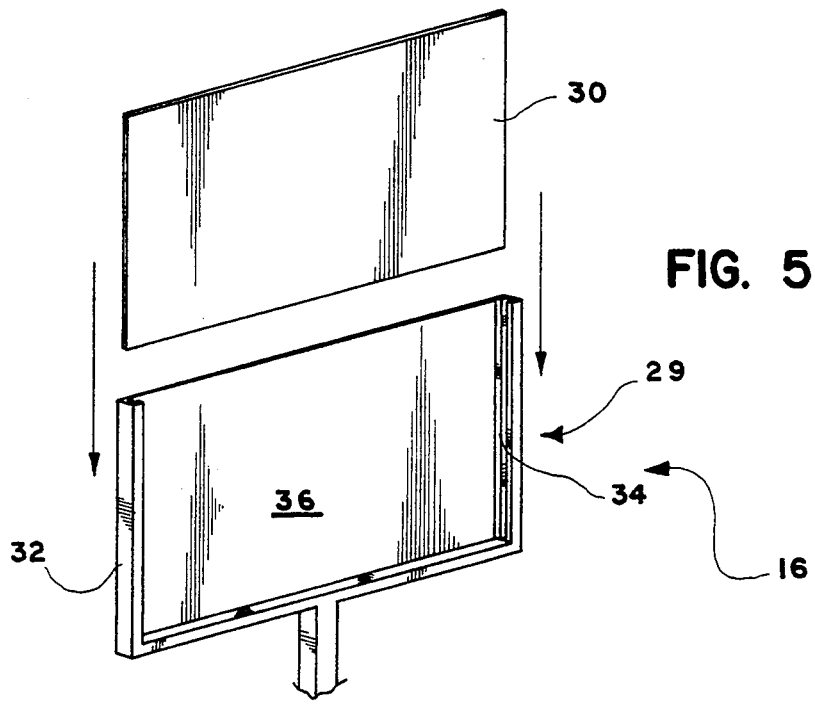
FIG. 5 is a perspective view showing a slidable engagement of the magnetic plate with the support body.

The support body 16 includes a frame 29 for supporting a magnetic plate 30, as is shown in FIG. 5, in which the surgical needle N is releasably engageable. Preferably, the frame 29 includes a U-shaped structure 32 having a track 34 therein for receiving the magnetic plate 30 and a backing plate 36 for providing supplemental support of the magnetic plate 30. The magnetic plate 30 is slidably engageable with the track 34 in the frame 29 and is gravitationally retained within the frame 29. A frictional fit may be provided between the frame 29 and the magnetic plate 30 to ensure that the magnetic plate 30 remains within the frame 29. The removal of the magnetic plate 30 permits the same to be sterilized (or disposed of) and replaced after use. The surgical needle system 10 in and of itself is fabricated so ass to be completed disposable so as to reduce the risk of spreading contamination.

Figure 6:
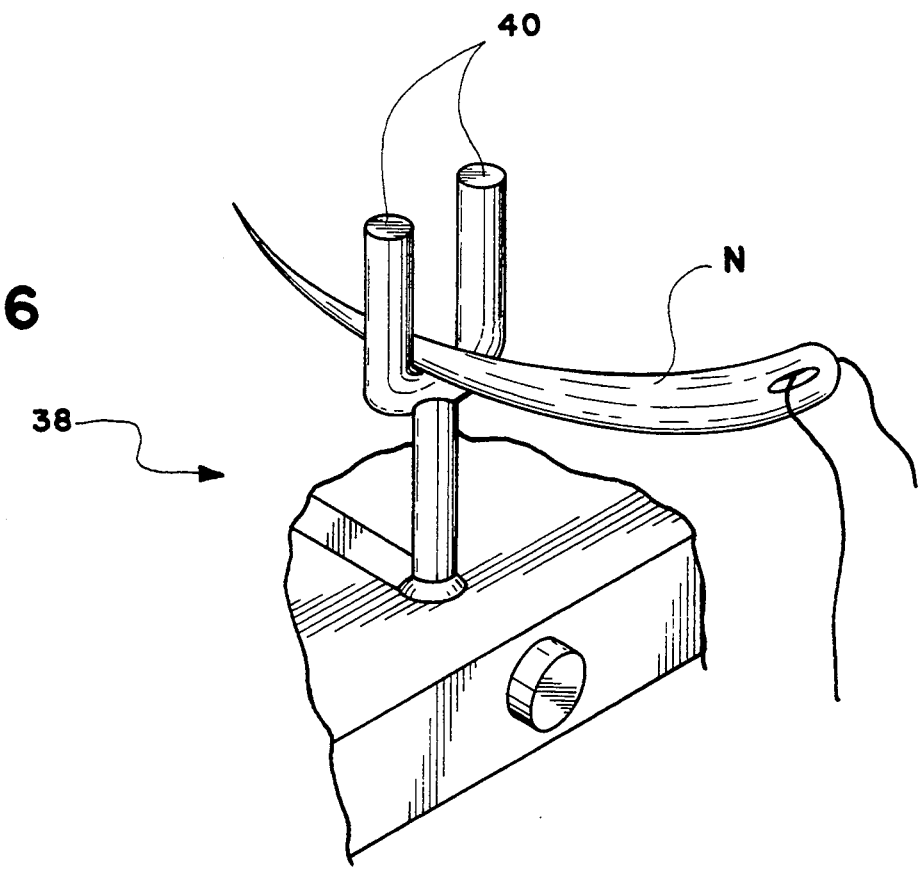
FIG. 6 is a perspective view of an alternative support body.

Alternatively, as is shown in FIG. 6, the support body 38 may include a pair of spaced apart prongs 40 which straddle the surgeon's needle N upon engagement therewith. Preferably, the support body 38 is dimensioned and configured to frictionally engage the needle N. The prongs 40 may also be of a magnetic material so as to retain the needle N therebetween via magnetic attraction.

Figure 7:
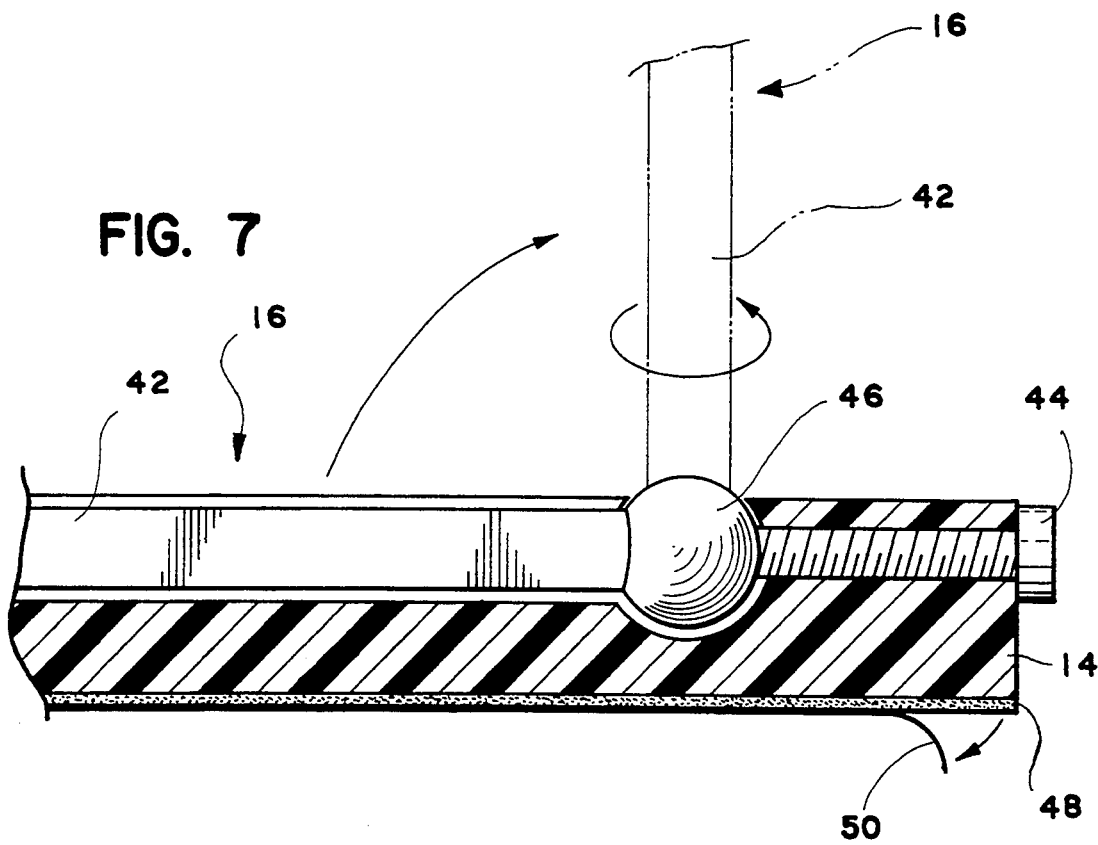
FIG. 7 is a detail view showing the engagement of the set screw with the ball at the terminal end of the shank of the support body.

As shown in FIG. 7, the support body 16 further include a shank 42 which terminates in the holder 14. The shank 42 terminates in a ball 46 which is movably mounted in the holder 14 such that the support body 16 is rotatable relative to the holder 14 about an axis of the shank 42 and is retractable within the holder 14 so as to maintain a low-profile when not in use. A set screw 44 is threadably engageable with the holder 14 as is adjustable to selectively engage the ball 46 at the terminal end of the shank 42 to set the support body 16 in a desired position. The support body 16 may be fully or partially retracted; fully extended to a position in a plane vertical to the upper surface of the holder 14; and rotatable about the axis of the shank 42; and may be set in the desired position via the set screw 44.

Shown in FIGS. 1, 2 and 7, the holder 14 has a lower surface which is covered with pressure sensitive adhesive 48 which, in turn, is covered with a protective plastic film 50. In use, the protective plastic film 50 is removed to expose the adhesive 48. The holder 14 is then positioned in a desired location on the wrist W where the same is held in contact with the wrist W via the adhesive 48. Once in position, the bracelet 12 is closed snugly about the wrist W. The adhesive 48 ensures that the bracelet 12 does not move about the wrist W of the surgeon.

It is to be understood that the present invention is not limited to the embodiments described above, but encompasses any and all embodiments within the scope of the following claims.

I claim:

1. A surgical needle system comprising:
   a bracelet for releasably attaching to a wrist;
   a holder supported by said bracelet;
   a support body for releasably engaging a surgical needle; and means for pivotally connecting said support body to said holder.

2. The surgical needle system according to claim 1, wherein said support body includes a magnetic element for releasably engaging the surgical needle.

3. The surgical needle system according to claim 2, wherein said support holder further includes a frame and said magnetic element is a magnetic plate slidably engageable with said frame.

4. The surgical needle system according to claim 1, wherein said support holder includes a pair of spaced apart prongs for engaging the surgeon's needle.

5. The surgical needle system according to claim 1, wherein said pivotally connecting means includes a ball and socket arrangement including a ball extending from said support body and means defining a socket within said holder, wherein
said ball is rotatably mounted in said socket.

6. The surgical needle system according to claim 1, wherein said support body includes an end surface provided with a shank which terminates in a ball, said ball being rotatably mounted in said holder to connect said support body to said holder.

7. The surgical needle system according to claim 6, further including a threaded set screw rotatably mounted in said holder, said set screw having sufficient length so as to engage said ball to fix said ball in a desired position.

8. The surgical needle system according to claim 1, wherein said holder includes a bottom surface having an adhesive coating thereon and a removable layer of protective film covering said adhesive coating.

9. The surgical needle system according to claim 1, wherein said bracelet includes portions of reduced cross-section to facilitate flexing of said bracelet.

10. A surgical needle comprising:
a flexible bracelet for releasably attaching to a wrist, said bracelet being severable so as to be adjustable to fit the wrist;
a holder for releasably engaging a surgical needle, said holder being supported by said bracelet; and
a support body movably engagable with said holder, wherein said support body includes a magnetic element.

11. The surgical needle system according to claim 10, wherein said support body includes a frame connected to said holder, wherein said magnetic element is supported in said frame.

12. The surgical needle system according to claim 10, wherein said support body includes a pair of spaced apart prongs movably connected to said holder, whereby
the surgeon's needle is releasably and frictionally engagable between said prongs.

13. The surgical needle system according to claim 10, wherein said support body has an end surface provided with a shank terminating in a ball, said ball being rotatably mounted in said holder, whereby
said support body is positionable in a vertical plane perpendicular to an upper surface of said holder.

14. The surgical needle system according to claim 13, wherein a threaded set screw is rotatably mounted in said holder, said set screw having sufficient length so as to engage said ball to fix said ball in a desired position.

15. The surgical needle system according to claim 10, wherein said bracelet has portions of reduced cross-section to facilitate flexing to conform to the wrist of the surgeon.

16. The surgical needle system according to claim 10, wherein said holder body has a lower surface which is covered with pressure sensitive adhesive which, in turn, is covered by a removable protective plastic film.

* * * * *

UNITED STATES PATENT AND TRADEMARK OFFICE
CERTIFICATE OF CORRECTION

PATENT NO. : 5,353,974
DATED : October 11, 1994
INVENTOR(S) : Maurizio Cortale, M.D.

It is certified that error appears in the above-indentified patent and that said Letters Patent is hereby corrected as shown below:

On the title page, item [76]: inventor name should read --Maurizio Cortale--

Signed and Sealed this

Twentieth Day of December, 1994

*Attest:*

BRUCE LEHMAN

*Attesting Officer*     *Commissioner of Patents and Trademarks*